(12) United States Patent
Psaltis et al.

(10) Patent No.: US 11,116,406 B2
(45) Date of Patent: Sep. 14, 2021

(54) DEVICE AND METHOD FOR INCREASED LIGHT TRANSMISSION THROUGH COCHLEAR BONE BY LASER ABLATION FOR IN SITU INTRACOCHLEAR IMAGING

(71) Applicants: ECOLE POLYTECHNIQUE FEDERALE DE LAUSANNE (EPFL), Lausanne (CH); MASSACHUSETTS EYE AND EAR INFIRMARY, Boston, MA (US)

(72) Inventors: Demetri Psaltis, Préverenges (CH); Konstantina Stankovic, Boston, MA (US); Donald Benjaman Conkey, Lonay (CH); Marilisa Romito, Lausanne (CH)

(73) Assignees: ECOLE POLYTECHNIQUE FEDERALE DE LAUSANNE (EPFL), Lausanne (CH); MASSACHUSETTS EYE AND EAR INFIRMARY, Boston, MA (US)

( * ) Notice: Subject to any disclaimer, the term of this patent is extended or adjusted under 35 U.S.C. 154(b) by 378 days.

(21) Appl. No.: 16/093,017

(22) PCT Filed: Apr. 13, 2017

(86) PCT No.: PCT/IB2017/052147
§ 371 (c)(1),
(2) Date: Oct. 11, 2018

(87) PCT Pub. No.: WO2017/179010
PCT Pub. Date: Oct. 19, 2017

(65) Prior Publication Data
US 2019/0200868 A1 Jul. 4, 2019

Related U.S. Application Data

(60) Provisional application No. 62/322,830, filed on Apr. 15, 2016.

(51) Int. Cl.
*A61B 1/00* (2006.01)
*A61B 5/00* (2006.01)
(Continued)

(52) U.S. Cl.
CPC .......... *A61B 5/0066* (2013.01); *A61B 5/0068* (2013.01); *A61B 5/0071* (2013.01);
(Continued)

(58) Field of Classification Search
CPC .............. A61K 2300/00; A61K 31/404; A61K 31/433; A61K 31/713; A61K 31/7105;
(Continued)

(56) References Cited

U.S. PATENT DOCUMENTS

| 4,408,602 A | 10/1983 | Nakajima |
| 2007/0055274 A1* | 3/2007 | Appenzeller ...... A61B 17/8858 606/90 |

(Continued)

FOREIGN PATENT DOCUMENTS

| EP | 2 749 234 | 7/2014 |
| WO | 2007/038975 | 4/2007 |

OTHER PUBLICATIONS

Bertolotti, J., et al., "Non-invasive imaging through opaque scattering layers," Nature, vol. 491, 2012, pp. 232-234.
(Continued)

*Primary Examiner* — Mark D Remaly
(74) *Attorney, Agent, or Firm* — Nixon & Vanderhye P.C.

(57) ABSTRACT

A method for visualizing structures inside a cochlea, comprising the steps of irradiating a cochlear bone with a first laser light to ablate portions of the cochlear bone, to form a thinned area of the cochlear bone, and imaging intracochlear
(Continued)

structures by a second light via the thinned area of the cochlear bone to optically scan targeted structures inside the cochlea.

8 Claims, 8 Drawing Sheets

(51) Int. Cl.
*A61B 18/20* (2006.01)
*A61B 17/00* (2006.01)
*A61B 18/00* (2006.01)

(52) U.S. Cl.
CPC .. *A61B 18/203* (2013.01); *A61B 2017/00057* (2013.01); *A61B 2018/00327* (2013.01); *A61B 2018/00577* (2013.01)

(58) Field of Classification Search
CPC .... A61K 38/1825; A61K 41/00; A61K 45/06; A61K 9/0009; A61K 9/0046; A61K 9/1647; A61K 9/5153; A61B 18/203; A61B 5/0066; A61B 2017/00057; A61B 2018/00327; A61B 2018/00577; A61B 5/0068; A61B 5/0071; A61F 11/04; A61F 2/04; A61N 2005/0605; A61N 5/0601; A61N 5/0622; A61P 27/16; A61P 43/00
See application file for complete search history.

(56) References Cited

U.S. PATENT DOCUMENTS

| | | | |
|---|---|---|---|
| 2008/0243127 A1 | 10/2008 | Lang et al. | |
| 2013/0060131 A1* | 3/2013 | Oghalai | A61B 5/0084 600/425 |
| 2015/0119785 A1* | 4/2015 | Kanu | A61F 13/38 604/3 |

OTHER PUBLICATIONS

Genina, Elina A., et al., "Optical Clearing of Cranial Bone," Advances in Optical Technologies, vol. 2008, Article ID 267867, 2008, 8 pages.

Hoy, Christopher L., et al., "Clinical Ultrafast Laser Surgery: Recent Advances and Future Directions," IEEE Journal of Selected Topics in Quantum Electronics, vol. 20, No. 2, Mar./Apr. 2014, pp. 242-255.

Jeong, Diana, et al., "Prospect for feedback guided surgery with ultra-short pulsed laser light," Current Opinion in Neurobiology, vol. 22, No. 1, Feb. 2012, pp. 24-33.

Lee, Hee Yoon, et al., "Noninvasive in vivo imaging reveals differences between tectorial membrane and basilar membrane traveling waves in the mouse cochlea," PNAS, vol. 112, No. 10, Mar. 10, 2015, pp. 3128-3133.

Macdonald, Glen H., et al., "Three-dimensional imaging of the intact mouse cochlea by fluorescent laser scanning confocal microscopy," Hearing Research, vol. 243, Nos. 1-2, Sep. 2008, pp. 1-10.

Papadopoulos, Ioannis N., et al., "High-resolution, lensless endoscope based on digital scanning through a multimode optical fiber," Biomedical Optics Express, vol. 4, No. 2, Feb. 1, 2013, pp. 260-270.

Popoff, S. M., et al., "Controlling light through optical disordered media: transmission matrix approach," New Journal of Physics, vol. 13, No. 12, 2011, 26 pages.

Tiede, LeAnn M., et al., "Determination of hair cell metabolic state in isolated cochlear preparations by two-photon microscopy," Journal of Biomedical Optics, vol. 12, No. 2, Mar./Apr. 2007, p. 021004-1-021004-8.

Tiede, LeAnn, et al., "Metabolic Imaging of the Organ of Corti—A Window on Cochlea Bioenergetics," Brain Research, vol. 1277, Jun. 24, 2009, pp. 37-41.

Vellekoop, I. M., et al., "Focusing coherent light through opaque strongly scattering media," Optics Letters, vol. 32, No. 16, Aug. 15, 2007, pp. 2309-2311.

Vogel, Alfred, et al., "Mechanisms of Pulsed Laser Ablation of Biological Tissues," Chemical Reviews, vol. 103, No. 2, 2003, pp. 577-644 and Additions and Corrections.

Vogel, A., et al., "Mechanisms of femtosecond laser nanosurgery of cells and tissues," Applied Physics B—Lasers and Optics, vol. 81, No. 8, 2005, pp. 1015-1047.

Wang, Ruikang K., et al., "Phase-sensitive optical coherence tomography imaging of the tissue motion within the organ of Corti at a subnanometer scale: a preliminary study," Journal of Biomedical Optics, vol. 15, No. 5, Sep./Oct. 2010, p. 056005-1-056005-9.

Yang, Guang, et al., "Thinned-skull cranial window technique for long-term imaging of the cortex in live mice," Nature Protocols, vol. 5, No. 2, Feb. 2010, pp. 201-208.

Yang, Xin, et al., "Two-photon microscopy of the mouse cochlea in situ for cellular diagnosis," Journal of Biomedical Optics, vol. 18, No. 3, Mar. 2013, p. 031104-1-031104-6.

Yaqoob, Zahid, et al., "Optical Phase Conjugation for Turbidity Suppression in Biological Samples," Nature Photonics, vol. 2, No. 2, 2008, pp. 110-115.

Zhu, Dan, et al., "Recent progress in tissue optical clearing," Laser & Photonics Reviews, vol. 7, No. 5, 2013, pp. 732-757.

Zipfel, Warren R., et al., "Nonlinear magic: multiphoton microscopy in the biosciences," Nature Biotechnology, vol. 21, No. 11, Nov. 2003, pp. 1369-1377.

International Search Report for PCT/IB2017/052147, dated Jul. 28, 2017, 5 pages.

Written Opinion of the ISA for PCT/IB2017/052147, dated Jul. 28, 2017, 6 pages.

* cited by examiner

BACKGROUND

BACKGROUND

BACKGROUND

DEVICE AND METHOD FOR INCREASED LIGHT TRANSMISSION THROUGH COCHLEAR BONE BY LASER ABLATION FOR IN SITU INTRACOCHLEAR IMAGING

The application is the U.S. national phase of International Application No. PCT/IB2017/052147 filed Apr. 13, 2017, which designated the U.S. and claims priority to the U.S. provisional patent application with the Ser. No. 62/322,830 that was filed on Apr. 15, 2016, the entire contents of each of which are incorporated by reference.

CROSS-REFERENCE FOR RELATED APPLICATIONS

The present application claims priority to the U.S. provisional patent application with the Ser. No. 62/322,830 that was filed on Apr. 15, 2016, the entire contents thereof herewith incorporated by reference.

FIELD OF THE INVENTION

The present invention relates to the field of in vivo imaging of the inner ear of a human patient, and methods for preparing the cochlea bone for the imaging of the inner ear.

DISCUSSION OF THE BACKGROUND ART

Sensorineural hearing loss (SNHL) is the most common type of hearing loss that affects more than 10% of the population worldwide. SNHL occurs when there is damage to the mechanosensory and neural structures inside the cochlea, or to the nerve pathways from the inner ear to the brain. Therefore, visualization within the cochlea would help diagnosing the status of the important intracochlear hearing structures. However, intracochlear imaging is extremely difficult due to the highly scattering cochlear bone and the difficulty of access. Current knowledge about human cochlear diseases is based on post mortem histopathologic analysis. Cochlear implants are the only hope for patients suffering from severe-to-profound hearing loss. To improve the existing situation, an intra-cochlear imaging technique is necessary for cellular-level diagnosis, study of pathophysiology, and treatment delivery and monitoring. Here, we propose a method to enable intracochlear imaging by thinning the cochlear bone. Bone thinning would allow a significant reduction of the scattering limitations, which include signal loss and image blurring when attempting to image through the intact cochlear bone.

A major cause of SNHL is damage to the intracochlear hair cells. Hair cells are a part of the organ of Corti, located inside the cochlea. They are the sensory receptors of the auditory system in all vertebrates and they detect movement in their environment through mechanotransduction. The cochlear bone has two natural openings: the round and the oval windows, as shown in FIG. 1A. The oval window is covered by a bony stapes footplate while the round window is sealed with a membrane that vibrates with opposite phase to vibrations of the stapes footplate. The movement of intracochlear fluids leads to stimulation of the hair cells of the organ of Corti, which leads to neurotransmitter release, excitation of the auditory nerve and transmission of impulses to the auditory cortex, resulting in hearing. In vertebrates the hair cells are organized as one row of inner and three rows of outer hair cells, as shown in FIG. 1B, depicting a cochlear cross section. Both hair cell types are uniformly distributed along the organ of Corti.

Currently, there is no in vivo technique for imaging within the human inner ear. The primary obstacle to intracochlear sensing and imaging is multiple scattering of light caused by biological tissues such as bone. The scattering compromises the focusing capability of an imaging system and the collection efficiency of the generated optical signal, for example the fluorescence emission. Furthermore, intracochlear imaging is particularly challenging because of the small dimension (<1 mm) of the cochlear chambers, the cochlea's complex, spiraling structure, the encasing dense cochlear bone, and the location with the bony skull base. Due to these challenges, modern cochlear therapeutics are relatively crude and essentially limited to hearing aids and cochlear implants. With the current lack of tools for intracochlear cellular-level diagnosis of hearing loss, an imaging method and module capable of capturing high-resolution images of the organ of Corti with minimal trauma would be beneficial to patients suffering from SNHL.

Modern optical microscopy techniques are being applied to cochleae to better understand hearing loss. Confocal microscopy is useful for its high resolution and contrast, but exogenous labelling makes it impractical for patient applications.[3] An additional technique that has been of interest lately in intracochlear imaging is two-photon excitation fluorescence (TPEF) microscopy.[4,5] TPEF is a nonlinear optical imaging technique with important advantages compared to conventional confocal microscopy,[6] such as deeper penetration into tissue due to the near-infrared excitation wavelength, reduced photo-damage, improved detection sensitivity, and optical sectioning. TPEF microscopy has also been used to examine metabolic events in the cochlear cells.[7] This can be done in response to stimuli known to cause hair cell loss, such as acoustic trauma and aminoglycoside administration. The observation was performed by viewing a small region through a hole drilled in the cochlear bone. Confocal and TPEF microscopy have been applied only in ex-vivo imaging of extracted cochleae. Optical coherence tomography (OCT) has been used in in vivo intracochlear imaging, although its application has been limited to mouse cochlea which have significantly thinner cochlear bone than humans.[1,2] Based on the above-discussed deficiencies of the background art, novel methods and systems are desired to perform in vivo imaging techniques of the human inner ear,

SUMMARY

According to one aspect of the present invention, a method for visualizing structures inside a cochlea is provided. Preferably, the method includes the steps of irradiating a cochlear bone with a first laser light to ablate portions of the cochlear bone, to form a thinned area of the cochlear bone, and imaging intracochlear structures by a second light via the thinned area of the cochlear bone to optically scan targeted structures inside the cochlea.

According to another aspect of the present invention, a system for removing bone from a cochlea is provided. Preferably, the system includes a laser ablation device providing focused laser pulses for removing bone structure to form a thinned area of the cochlear bone, and an optical coherence tomography device to measure a bone thickness of the thinned area of the cochlear bone.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the representations are simplified for illustration purposes and may not be depicted to scale.

BRIEF DESCRIPTION OF THE SEVERAL EMBODIMENTS

Figure 1A:
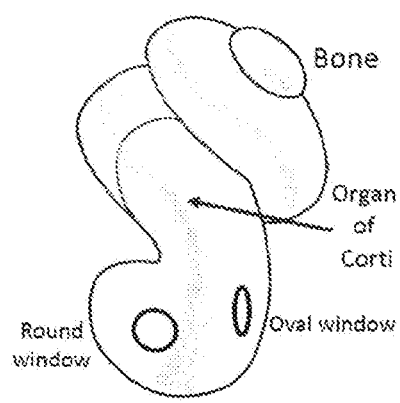
FIG. 1A shows a schematic side-view representation of the cochlear bone.
Figure 1B:
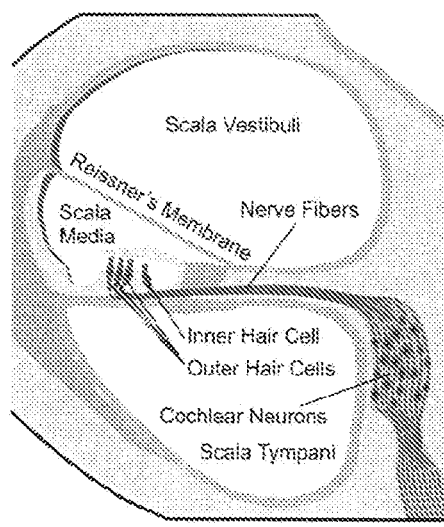
FIG. 1B shows a schematic cross-sectional view of an interior of the cochlear bone.
Figure 2:
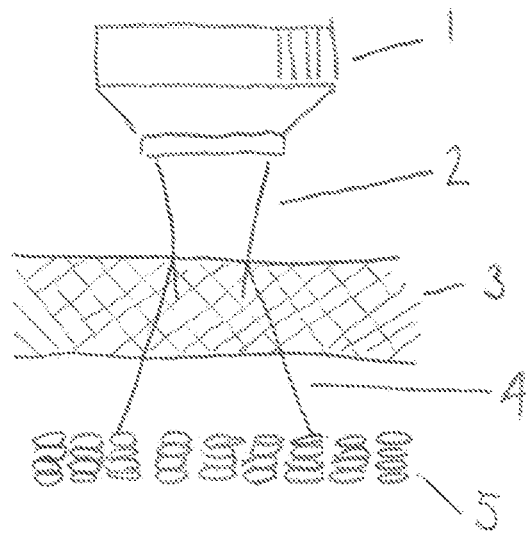
FIG. 2 shows a schematic side view of an background optical imaging device for imaging through a bone causing scattered light of the imaging light.

In the present application, a method, system, and device is proposed that uses a focused laser pulse to selectively thin the cochlear bone with laser ablation technique to significantly reduce scattering in front of the organ of Corti when using an imaging device. This method is not limited to organ of Corti imaging, but could also be utilized to image other intracochlear structures, including and not limited to Reissner's membrane, fibrocytes of the spiral ligament, vessels within the stria vascularis, supporting cells of the organ of Corti, cochlear neurons, Schwann cells. Without the bone thinning by the laser ablation technique, optical imaging is severely restricted by optical scattering in the bone, as shown in FIG. 2. As further shown in FIG. 2, when an imaging device 1 delivers a focused laser beam 2 to the bone 3, the light no longer focuses but is scattered 4. As a result, the focus cannot be delivered to the imaging target 5 and no image can be obtained. According to the present method and system, by reducing the thickness of the scattering layer, i.e. the bone layer, the amount of scattering can be significantly reduced to the extent that an image can be obtained. Thinning the bone 3 would allow for a significant increase in the intensity of transmitted light through the tissue and enable high resolution optical imaging through the tissue barrier. Similar methods have been used to image the brain through the skull of mice.[8,9] Integration of an optical imaging device to the thinned cochlear bone could then be used for intracochlear imaging. Aspects of the present invention presents several variations of the ablation and imaging methods for this in vivo imaging technique.

The publication to Yang et al. discussed two-photon excitation microscopy (TPEF) imaging of the mouse hair cells in three-dimensionally intact, unstained cochleae, with intact cochlear bone.[5] In that study, mouse cochleae were imaged without exogenous dyes through the membranous round window using a near-infrared femtosecond laser as the excitation and endogenous TPEF and second harmonic generation as the contrast mechanisms. The TPEF results through the round window exhibited strong contrast, allowing cellular- and even subcellular-resolution imaging and detection of pathologic changes, and they motivated the development of a diagnostic tool based on fiber-microendoscopy. While Yang et al. demonstrated the possibility of imaging the organ of Corti through the round window, they also showed that imaging through the round window provided a limited diagnostic field of view. Specifically, imaging adjacent to the round window provides information about the cochlear base, which encodes high-frequencies, but not about the cochlear regions encoding mid- and low-frequency sounds that are important for understanding of speech. Furthermore, the anatomy of the ear and the position of the round window pose important challenges on the design of instruments required to image intracochlear structures via the external ear canal. For example, the human organ of Corti is about 500 μm away from the round window membrane, and at a 44° viewing angle from the round window membrane. These challenges discussed above with respect to Yang et al. has motivated the use of an alternative access route for future in vivo imaging of the organ of Corti.

According to one aspect of the present invention, in the present method or system the bone is modified for enhanced imaging. Laser ablation provides a mechanism for high-precision removal of bone material. The physical effect which causes the ablation depends on the material and laser properties, including wavelength, pulse duration, and pulse energy.[10] The ablation mechanism can be broadly separated into plasma-mediated techniques and thermal ablation techniques. Plasma-mediated ablation has a smaller ablation volume, but higher precision then thermal ablation techniques. Other parameters affecting the ablation of material are the pattern with which the focused beam scans the surface, the repetition rate of the laser pulses, the speed of the scanning beam, the energy of the laser pulse, the focusing numerical aperture of the ablation beam. According to one aspect, the ablation modalities are presented, bony wall structures, ablation devices, and a system for monitoring the ablation for bone structural modification.

Regarding the plasma-mediated ablation, the ablation occurs as laser irradiance surpasses an optical breakdown threshold over which multiphoton ionization leads to plasma formation.[10-12] The high irradiance can be achieved with lower energy in an ultrafast pulse, for example smaller than 10 ps. With an ultrafast pulse most of the additional pulse energy beyond threshold feeds a rapidly growing plasma, thus minimizing heat accumulation and thermal damage beyond the focal volume. The nonlinear, multiphoton interaction that drives the plasma-mediated ablation also provides high three-dimensional confinement and precision.[11,12]

Regarding the thermal ablation, this ablation technique uses pulse durations in the nanosecond and microsecond range rely on the absorptive properties of the material. The absorbed optical energy heats and eventually ablates the material through evaporation or sublimation of the material.

The thermal process allows for a much larger interaction zone and larger ablation volume than the plasma process at the expense of precision.[10]

For the cochlear bone thinning, according to an aspect of the present invention, the high precision and low collateral damage of laser ablation allows for the controlled removal of the cochlear bone. The structural modification which could be attained with the laser ablation for increased photon transmission through the bone are outlined here.

Figure 3A:
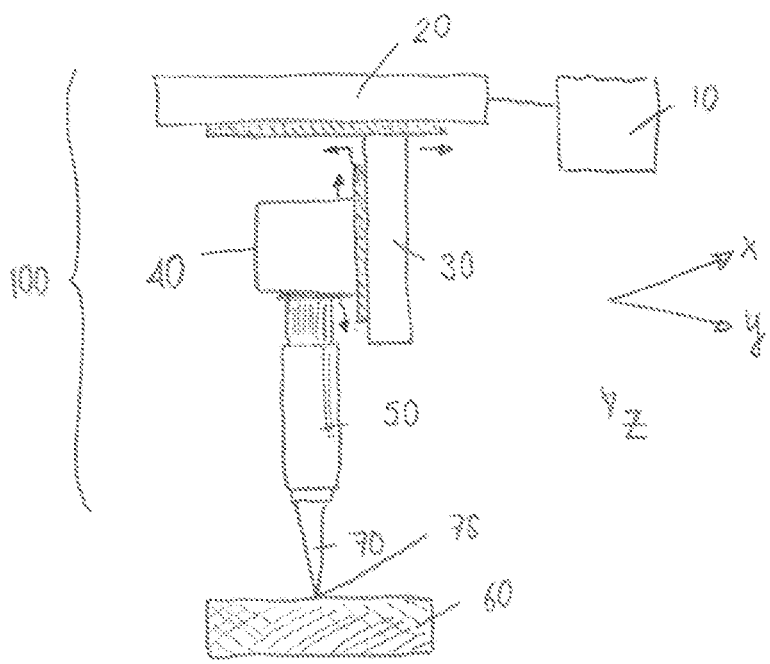
FIGS. 3A and 3B shows schematic side views of an exemplary laser ablation device 100 for removing bone, with FIG. 3A showing the beginning of the process, and FIG. 3B showing the removal of bone.
Figure 3B:
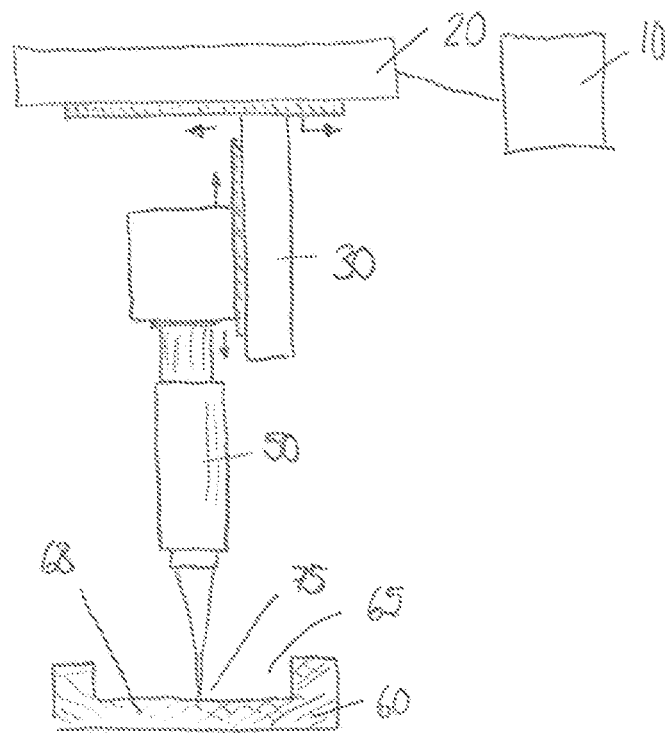

To decrease the scattering of light in the cochlear bony wall and increase photon transmission throughput, the bone may be thinned with laser ablation. FIGS. 3A and 3B shows schematic side views of an exemplary laser ablation device 100 having a controller 10, an XY translation stage 20, a Z translation stage 30 operatively mounted to the XY translation stage 20, a laser light source 40 mounted to the Z translation stage 30, optics 50 for focusing laser beam 70 in a focusing point 75 on a surface of bone 60, for example the cochlea. FIG. 3A shows the laser ablation device 100 before any bone has been removed, at a starting moment for the ablation. As shown in FIG. 3B, bone material has been removed to form bone opening 65 and thinned portion 68. Scanning the focused laser beam 70 across the surface allows for selective removal of bone material from bone 60. Each pass across a surface removes a specific depth of bone dependent on the laser irradiance in the focus, the pulse duration, focus spot size, and focal depth. Additional scans across the deepening surface will further increase the volume of ablated bone, to form a bone opening 65 to form a thinned-out portion 68 of the bone.

Figure 4A:
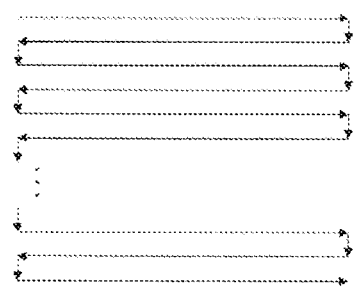
FIGS. 4A to 4D show top views in a Z direction of variety of laser focus scanning patterns along the X and Y direction for bone removal by laser ablation.
Figure 4B:
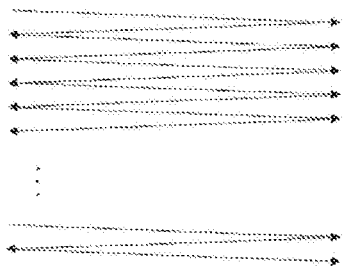
Figure 4C:
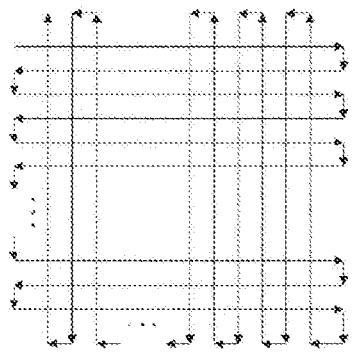
Figure 4D:
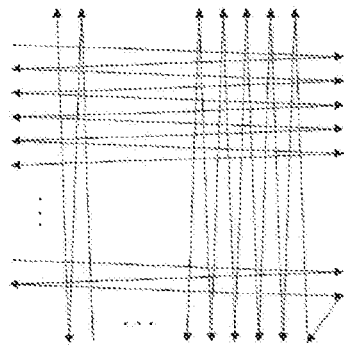

FIGS. 4A to 4D show top views in a Z direction of variety of laser focus scanning patterns along the X and Y direction which may be used across the bone surface to optimize ablation speed or surface smoothness. For example, FIG. 4A shows a scanning pattern wherein a step movement is used in the Y direction to move to an adjacent line and the X direction reversed. The separation between parallel ablation lines is selected to ensure complete removal of material and minimize surface roughness. FIG. 4B shows a pattern which utilizes a constant velocity in the Y direction. The velocity would be selected such that an acceptable separation in line spacing in the Y direction would be realized after traveling the full range in the X direction. This allows for total coverage of the targeted surface for complete removal of material. The parameters could be optimized to minimize the surface roughness. The patterns shown in FIGS. 4A and 4B can be used to create a cross hatch in which the same pattern is ablated a second time, only rotated by 90 degrees, as shown in FIGS. 4C and 4D. Lissajous patterns, spiral patterns, or other types of patterns that cover the targeted area in the bone could also be applied. Further variations to the pattern could be applied by modifying the repetition rate and pulse overlap during the ablation process.

Before the laser ablation is performed, for example as shown in FIG. 3B using the laser ablation device 100, it is possible to use an imaging or sensing device configured to measure or scan the surface of the bone 60 to select the appropriate laser ablation location and a pattern which conforms to the bone topography. In this measuring step, the imaging and sensing device could also be configured to measure a thickness of the bone 60, or the photon transmission through or backscattered light from the bone 60 to provide feedback to the bone modification process to avoid complete removal of the bony wall. For example, optical coherence tomography (OCT) could be used to measure bone thickness and photon transmission information through bone 60. Other fluorescence imaging modalities could provide structural information as well.

Figure 5:
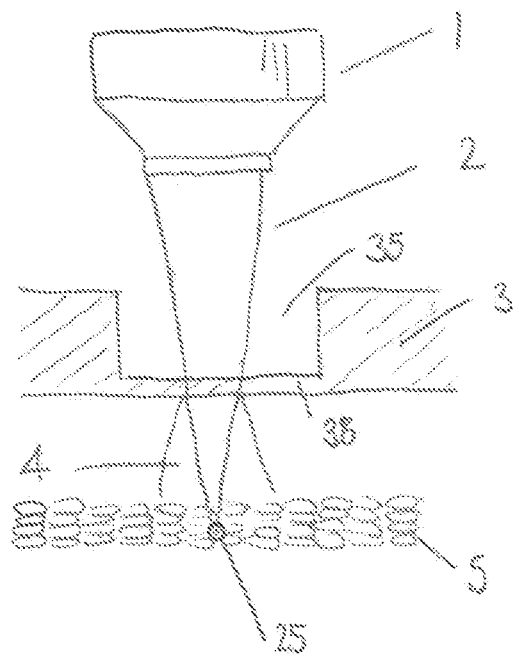
FIG. 5 shows a simplified side view of an imaging device for performing in vivo cochlea imaging.
Figure 6A:
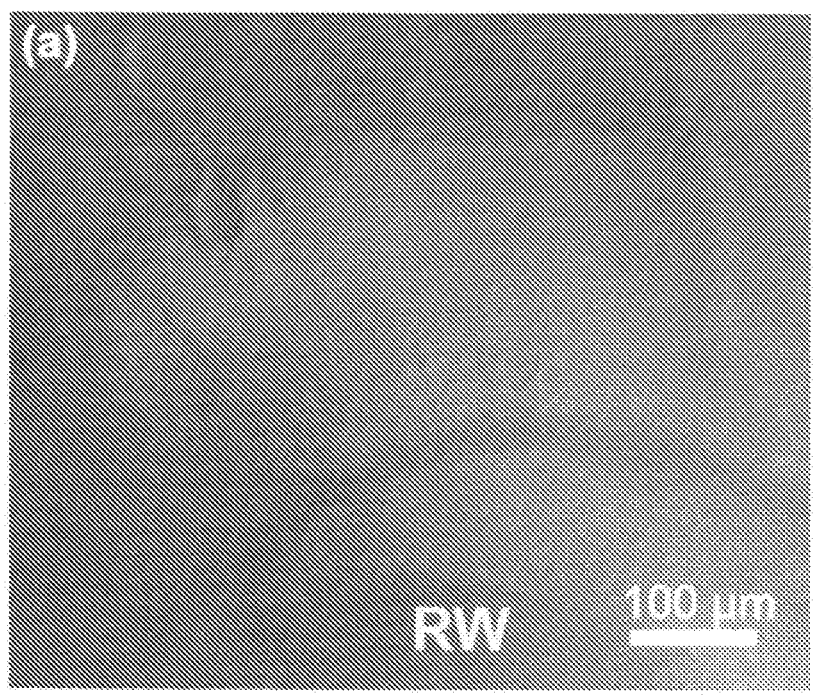
FIGS. 6A to 6D show experimental results and images of cochlear bone thinning and the subsequent imaging.
Figure 6B:
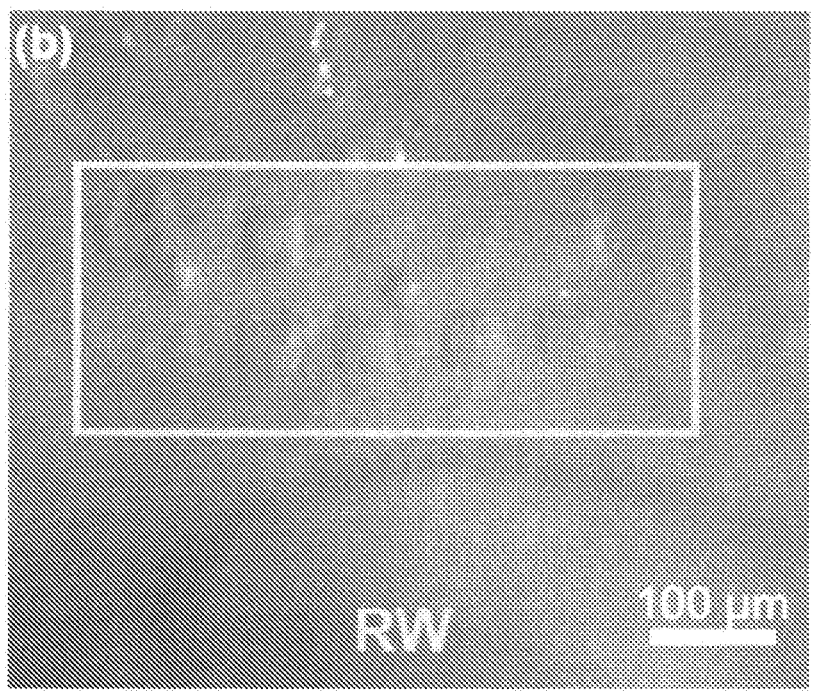
Figure 6C:
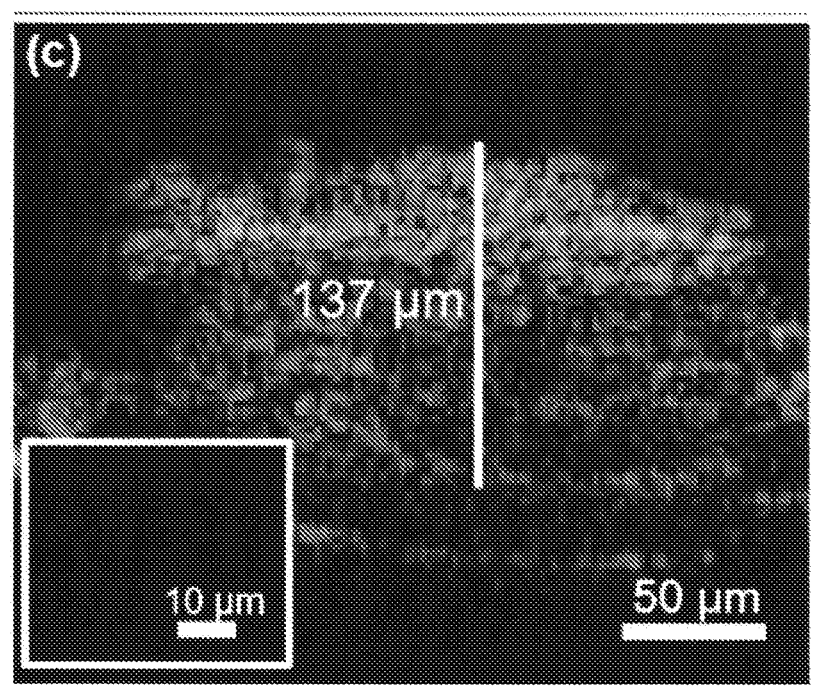
Figure 6D:
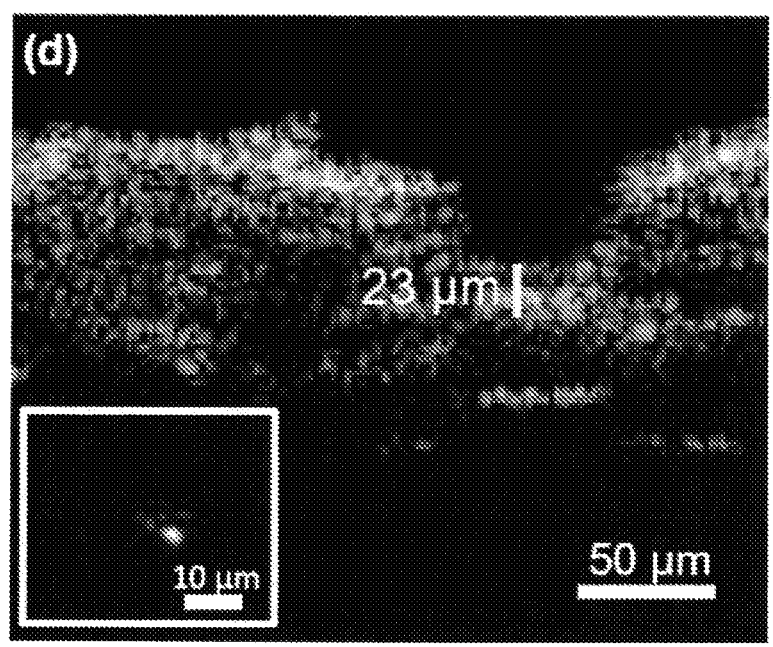

Next, the method includes a step of performing the imaging of the interior of the cochlea. A simplified imaging device is shown in a schematic side view in FIG. 5. Because the bone 3 has been thinned to form thinned portion 38 and bone opening 35, an imaging device 1 can be employed to image the intracochlear structures. For example, an imaging device 1 delivers a focused laser beam 2 with a focusing point 25 in the tissue or target structures 5. With the bone thinned at thinned portion 38, the incident beam undergoes significantly less beam scattering 4 and more photons arrive in the focal region or focusing point 25 on the targeted structures 5. Several optical imaging methodologies could be utilized with this technique, including methods for improving the optical focus quality through the now-thinned bone. Scanning imaging techniques which require the delivery of a focused laser beam on the targeted structures for imaging FIGS. 6A to 6D show experimental results and images of cochlear bone thinning and subsequent imaging and experimentally illustrates results of the imaging concept shown in FIG. 5. FIG. 6A shows a mouse cochlea bone next to the round window (RW) before ablation. FIG. 6B shows ten (10) sections of ablated regions on the cochlea bone. Each ablated region has a surface area of 50 µm×50 µm and has been ablated to different depths with a 3.2 µJ focused laser beam with pulse width 1 ps. FIG. 6C shows an OCT B-scan, the cross section showing transversal and axial dimensions of a mouse cochlea before ablation, showing a thickness of 137 µm. FIG. 6D shows the OCT B-scan of a mouse cochlea bone after ablation. the bone has been thinned to 23 µm. The insets of FIGS. 6C and 6D show the transmission of a focused laser beam through the respective cochlear bones. Without bone thinning the transmission is minimal and unfocused, however after thinning a focus is transmitted.

Next, in accordance to some other aspects of the present invention, several possible imaging situations will be presented, including methods for improving focal spot quality and fluence, the various imaging modalities which may be applied, and an exemplary imaging device is discussed.

According to another aspect of the present invention, before performing the imaging of the interior of the cochlea, a step of optical clearing is performed to reduce the scattering of light by the tissue, and to increase its transparency. Some of these features is discussed in Zhu et al., "Recent progress in tissue optical clearing," Laser Photonics Review, Vol. 7, pp. 732-757, 2013, this reference being herewith incorporated by reference in its entirety. In this step, an optical clearing agent applied within a scattering tissue will more closely match the index of refraction of the light scattering particles within a material. For example, as shown in Genina et al., "Optical Clearing of Cranial Bone," Advances in Optical Technologies, e267867 (2008), this reference herewith incorporated by reference in its entirety, glycerol can be used as an optical clearing agent in cranial bone, and in the present method in the cochlea, and has been shown to reduce the scattering coefficient by 30%. In the present method, an optical clearing agent can be applied to the thinned bony wall, for example thinned bone portion 38 or 68, after ablation to further decrease the light scattering of the bony wall and improve image quality.

Moreover, according to another aspect of the present invention, it is possible to use optical phase conjugation and wavefront shaping when performing the step of imaging. With wavefront shaping, it is possible to perform light control through scattering materials, in the present case the thinned cochlear bone. In this way a scattered light field can be measured and compensated to adjust for scattering that is caused by the cochlear bone, to substantially remove or reduce the scatter effects in the image, and improve focus quality and intensity.[15-17] There are many methods for doing this, including iterative,[15] optical phase conjugation,[18] and transmission matrix approaches.[17]

According to another aspect of the present invention, different imaging modalities or imaging devices may be applied through the thinned bony wall, for example thinned wall 38, 68. Specifically, fluorescence microscopy, confocal, two photon fluorescence, second harmonic generation, or optical coherence microscopy can be used as they apply a focused laser beam. Even speckle scanning techniques or wide field imaging methods may be applied.[19] For performing the imaging of structures inside the cochlea, the imaging device is an endoscope device for imaging within the inner ear specifically utilized for imaging. These include, but are not limited to, multimode fiber endoscopes,[20] multicore fiber endoscopes, fiber bundles, gradient-index (GRIN) lens and optics, or other optical designs.

Figure 7:
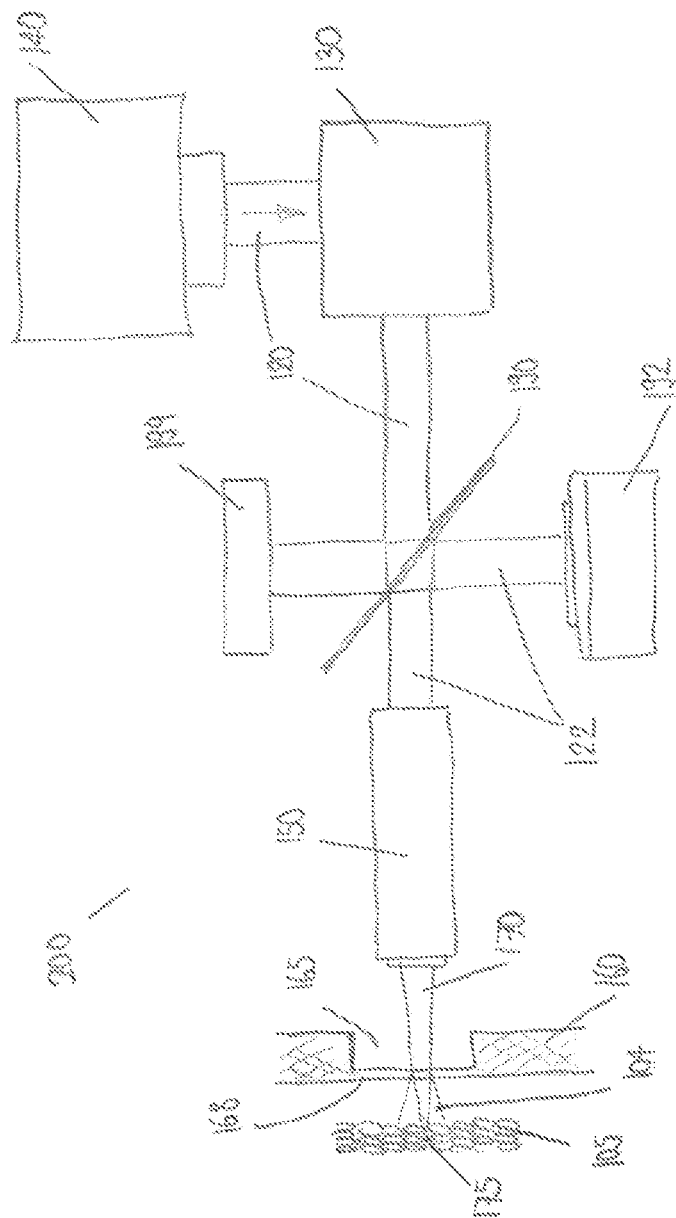
FIG. 7 shows a schematic representation for an exemplary imaging device or system 200.

FIG. 7 shows a schematic representation for an exemplary imaging device or system 200, according to an aspect of the present invention. A light source 140, such as a device using a laser, a light-emitting diode, or superluminescent diode, or other type of illumination, emits a beam of light 120 used for imaging. Using a combination of a scanning system 130 and an endoscope 150, the beam is focused 170 through the bone 160 which has been thinned to form a thinned portion 168 by an opening 165 to form a focusing point 175 in the imaging target 175 via the thinned portion 168, and then scanned by scanning system 130. Some scattered light 104 will be caused when the focused beam 170 passes via the thinned portion 168. The scanning system 130 can be but is not limited to galvanometric mirrors or a spatial light modulator. For example, endoscope 150 can be a multimode fiber, multicore fiber, fiber bundle, GRIN lens, or any device capable of delivering focused light to the cochlea, indicated as bone 160, onto the imaging target 105. After the imaging light interacts with imaging target 105 and is reflected back towards endoscope 150, target light 122 is collected by the endoscope 150 and separated from the optical path of the imaging light 120 with a beamsplitter 190 and directed towards photodetector 192, to be detected by photodetector 192.

The nature of the target light 122 will depend on the imaging modality being used. For example, in fluorescence microscopy such as confocal fluorescence, two-photon fluorescence, or second harmonic generation, target light 122 will be emitted at a different wavelength than the imaging light 120. In this case, the beamsplitter 190 could be a dichroic mirror to separate the light at different wavelengths. In reflection-based microscopy, such as confocal reflection or optical coherence tomography (OCT), the light will have the same wavelength. For OCT, a reference arm 194 would also be necessary which would match the optical path length and dispersion of the arm formed by the endoscope 150.

Moreover, after imaging, the modified structure of the bone 30, 60 can be reinforced with a bone cement or another material to aid healing, by filling the opening 35, 65 with a bone cement.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

REFERENCES

1. Lee, H. Y. et al. Noninvasive in vivo imaging reveals differences between tectorial membrane and basilar membrane traveling waves in the mouse cochlea. *Proc. Natl. Acad. Sci.* 112, 3128-3133 (2015).
2. Wang, R. K. & Nuttall, A. L. Phase-sensitive optical coherence tomography imaging of the tissue motion within the organ of Corti at a subnanometer scale: a preliminary study. *J. Biomed. Opt.* 15, 056005-056005-9 (2010).
3. MacDonald, G. H. & Rubel, E. W. Three-dimensional imaging of the intact mouse cochlea by fluorescent laser scanning confocal microscopy. *Hear. Res.* 243, 1-10 (2008).
4. Tiede, L. M., Rocha-Sanchez, S. M., Hallworth, R., Nichols, M. G. & Beisel, K. Determination of hair cell metabolic state in isolated cochlear preparations by two-photon microscopy. *J. Biomed. Opt.* 12, 021004-021004-8 (2007).
5. Yang, X. et al. Two-photon microscopy of the mouse cochlea in situ for cellular diagnosis. *J. Biomed. Opt.* 18, 031104-031104 (2012).
6. Zipfel, W. R., Williams, R. M. & Webb, W. W. Nonlinear magic: multiphoton microscopy in the biosciences. *Nat. Biotechnol.* 21, 1369-1377 (2003).
7. Tiede, L., Steyger, P. S., Nichols, M. G. & Hallworth, R. Metabolic imaging of the organ of corti—A window on cochlea bioenergetics. *Brain Res.* 1277, 37-41 (2009).
8. Yang, G., Pan, F., Parkhurst, C. N., Grutzendler, J. & Gan, W.-B. Thinned-skull cranial window technique for long-term imaging of the cortex in live mice. *Nat. Protoc.* 5, 201-208 (2010).
9. Jeong, D. C., Tsai, P. S. & Kleinfeld, D. Prospect for feedback guided surgery with ultra-short pulsed laser light. *Curr. Opin. Neurobiol.* 22, 24-33 (2012).
10. Vogel, A. & Venugopalan, V. Mechanisms of Pulsed Laser Ablation of Biological Tissues. *Chem. Rev.* 103, 577-644 (2003).
11. Hoy, C. L. et al. Clinical Ultrafast Laser Surgery: Recent Advances and Future Directions. *IEEE J. Sel. Top. Quantum Electron.* 20, 242-255 (2014).
12. Vogel, A., Noack, J., Wittman, G. & Paltauf, G. Mechanisms of femtosecond laser nanosurgery of cells and tissues. *Appl. Phys. B* 81, 1015-1047 (2005).
13. Zhu, D., Larin, K. V., Luo, Q. & Tuchin, V. V. Recent progress in tissue optical clearing. *Laser Photonics Rev.* 7, 732-757 (2013).
14. Genina, E. A., Bashkatov, A. N. & Tuchin, V. V. Optical Clearing of Cranial Bone. *Adv. Opt. Technol.* 2008, e267867 (2008).
15. Vellekoop, I. M. & Mosk, A. P. Focusing coherent light through opaque strongly scattering media. *Opt. Lett.* 32, 2309-2311 (2007).
16. Yaqoob, Z., Psaltis, D., Feld, M. S. & Yang, C. Optical phase conjugation for turbidity suppression in biological samples. *Nat. Photonics* 2, 110-115 (2008).
17. Popoff, S., Lerosey, G., Fink, M., Boccara, A. C. & Gigan, S. Controlling Light Through Optical Disordered Media: Transmission Matrix Approach. 1107.5285 (2011).
18. Yaqoob, Z., Psaltis, D., Feld, M. S. & Yang, C. Optical phase conjugation for turbidity suppression in biological samples. *Nat Photon* 2, 110-115 (2008).

19. Bertolotti, J. et al. Non-invasive imaging through opaque scattering layers. *Nature* 491, 232-234 (2012).
20. Papadopoulos, I. N., Farahi, S., Moser, C. & Psaltis, D. High-resolution, lensless endoscope based on digital scanning through a multimodeoptical fiber. *Biomed. Opt. Express* 4, 260-270 (2013).

The invention claimed is:

1. A method for visualizing structures inside a cochlea, comprising the steps of:
   irradiating a cochlear bone with a first laser light to ablate portions of the cochlear bone, to form a thinned area of the cochlear bone; and
   imaging intracochlear structures by optical coherence tomography with a second light via the thinned area of the cochlear bone to optically scan targeted structures inside the cochlea.

2. The method according to claim 1, further comprising the step of:
   measuring a thickness of the thinned area of the cochlear bone with the optical coherence tomography.

3. The method according to claim 1, further comprising the step of:
   applying an optical clearing agent to the cochlear bone before the step of imaging.

4. The method according to claim 1, further comprising the step of:
   filling the thinned area of the cochlear bone with a bone cement, after the step of imaging.

5. The method according to claim 1, further comprising the step of:
   measuring and compensating for scattered light caused by the thinned area of the cochlear bone to adjust scatter and improve focus quality and intensity of the second light.

6. The method according to claim 1, wherein the step of irradiating and the step of imaging are performed in vivo.

7. A system for removing bone from a cochlea, comprising:
   a laser ablation device providing focused laser pulses for removing bone structure to form a thinned area of the cochlear bone; and
   an optical coherence tomography device to measure a bone thickness of the thinned area of the cochlear bone.

8. The system according to claim 7, wherein the focused laser pulses are smaller than 10 ps.

* * * * *